Figure 1:
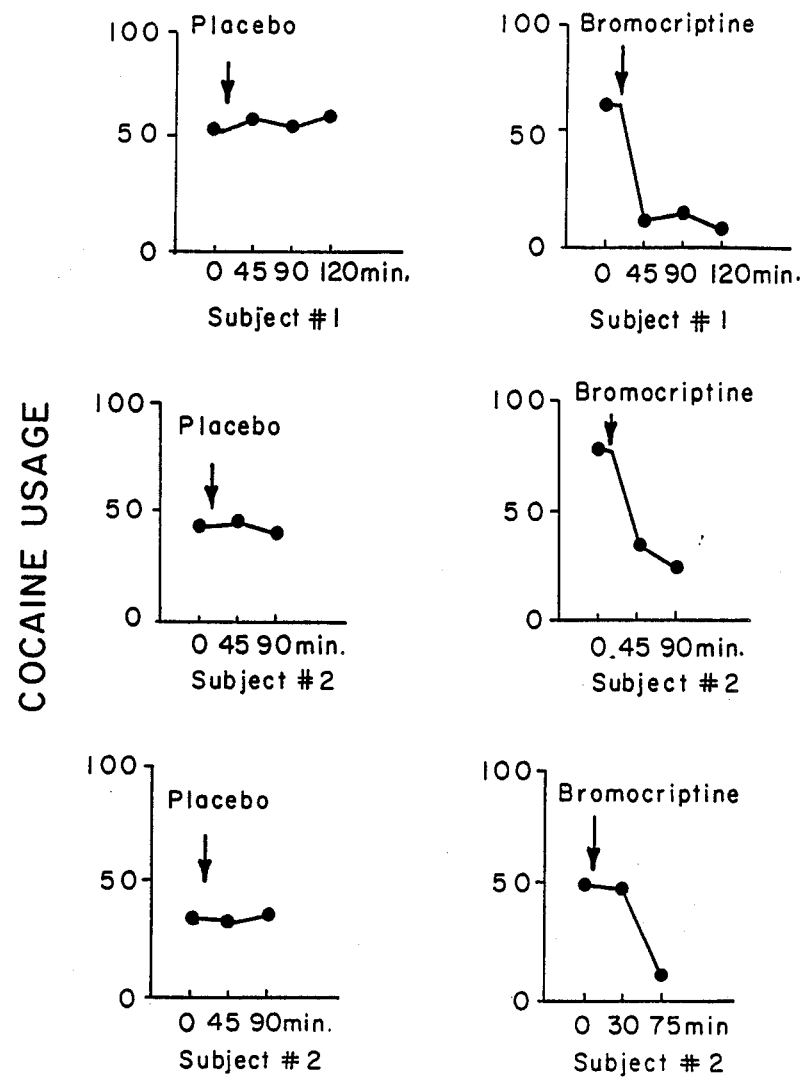

United States Patent [19]

Dackis et al.

[11] Patent Number: 4,935,429

[45] Date of Patent: Jun. 19, 1990

[54] METHOD OF TREATING PSYCHOSTIMULANT ADDICTION

[76] Inventors: Charles A. Dackis, 96 Joan Dr., Watchung, N.J. 07060; Mark S. Gold, 145 Forest Dr., Short Hills, N.J. 07078

[21] Appl. No.: 260,860

[22] Filed: Oct. 21, 1988

Related U.S. Application Data

[63] Continuation of Ser. No. 123,013, Nov. 19, 1987, abandoned, which is a continuation of Ser. No. 36,602, Apr. 10, 1987, abandoned, which is a continuation of Ser. No. 857,690, Apr. 30, 1986, abandoned, which is a continuation-in-part of Ser. No. 731,102, May 6, 1985, abandoned, and Ser. No. 791,188, Oct. 25, 1985, abandoned.

[51] Int. Cl.$^5$ .................. A61K 31/44; A61K 31/135; A61K 31/195

[52] U.S. Cl. ................................. 514/288; 514/561; 514/646; 514/812

[58] Field of Search ................ 514/288, 561, 646, 812

*Primary Examiner*—Stanley J. Friedman
*Attorney, Agent, or Firm*—Gerald D. Sharkin; Robert S. Honor; Thomas O. McGovern

[57] ABSTRACT

A method of treating psychostimulant abuse with a therapeutically effective amount of a dopamine agonist.

32 Claims, 1 Drawing Sheet

METHOD OF TREATING PSYCHOSTIMULANT ADDICTION

This is a continuation of application Ser. No. 07/123,013, filed Nov. 19, 1987, which in turn is a continuation of application Ser. No. 036,602, filed Apr. 10, 1987, now abandoned, which in turn is a continuation of application Ser. No. 06/857,690, filed Apr. 30, 1986, now abandoned, which in turn is a continuation-in-part of Ser. No. 06/731,102, filed May 6, 1985, now abandoned, and Ser. No. 791,188, filed Oct. 25, 1985, now abandoned.

This invention relates to a new method of treating central or psychostimulant addiction. More particularly, it relates to a method of inhibiting or eliminating withdrawal symptoms in humans undergoing treatment for central or psychostimulant abuse and to a method of preventing craving after withdrawal by the administration of a dopamine agonist.

Psychostimulant abuse has grown rapidly over the years, evolving into a major medical and social problem. The most commonly abused psychostimulants are cocaine, amphetamine, methamphetamine, dextroamphetamine, pemoline and their pharmaceutically acceptable acid addition salts such as the phosphate, sulphate, 4-chlorophenoxyacetate and the like.

In the case of cocaine, abuse has grown rapidly over the past several years, evolving into a major medical and social problem with far reaching effects It is estimated that, while already 22 million Americans have used cocaine, initial and compulsive use continues to soar at a rapid rate. Contrary to popular myths regarding the safety of cocaine, this increased use has led to a threefold rise in emergency room visits, a fourfold increase in deaths and a sixfold increase in hospitalization between 1976 and 1981.

Medical complications of cocaine use comprise only one element of this hazardous practice. Financial, legal, social and vocational deterioration often occurs as compulsive cocaine use becomes the user's highest priority. A random survey of 500 users found that 67% were male and 33% female; ages ranged from 22 to 59 years, with a mean of 30 years; and 85% were white and 15% were black or Hispanic. The mean level of education was fairly high, at 14.1 years, and 40% had annual incomes over $25,000. Estimates of the amounts of cocaine used ranged from 1 to 32 grams per week. The frequency of use averaged 5.7 days per week, with 48% taking the drug daily. At prices of $100 to $125 per gram, the average amount of money spent per week on cocaine was over $637, with a range from $100 to $3,250. Sixty-six percent of those interviewed said that they felt addicted to cocaine; 75% said that they had lost control over cocaine use; and 83% said that they were unable to refuse cocaine when it was available. Despite repeated attempts to stop cocaine use, 67% said that they were unable to stay away from cocaine for as long as one month.

Abrupt cessation of chronic high-dose use of psychostimulants can result in a variety of undesirable physical symptoms Cocaine withdrawal, for instance, does not produce a stereotyped abstinence syndrome as with opiates or barbiturates. However, abrupt cessation of chronic high dose use can induce symptoms including: drug craving, depression, irritability, anergia, amotivation, appetite changes, nausea, shaking, psychomotoric retardation and irregular sleep patterns hypersomia that may persist for a week or longer following cessation of use. Relief of these symptoms would allow patients to stop using psychostimulants more easily and would also be useful in the post-drug recovery period.

It has been widely reported that cocaine is a potent inhibitor of dopamine reuptake and appears to cause accute increases in dopamine transmission. Dopaminergic neurons also appear to mediate the euphoric response to cocaine and are critical in the development of addiction. There are certain effects of cocaine, which depend on the integrity of the dopaminergic systems. Animals, in which a lesion in the nucleus accumbens is produced by the dopamine toxin 6-hydroxy-dopamine, stop self-administering cocaine. However, even though cocaine at first increases dopamine transmission and concentration, a functional reduction in dopaminergic activity appears to follow administration of the drug.

It has also been reported that dopamine receptor agonists, such as apomorphine and piribedil, have amphetamine-like rewarding action in animals. Conversely, selective dopamine receptor antagonists reduce or eliminate both electrical and central stimulant self-administration by animals. The antagonist pimozide initially caused animals to increase lever pressing for amphetamine at low doses; but at increased doses, it obliterated the self-administration of amphetamine. These results illustrate the part played by dopamine in the mechanism of reward.

It is now proposed that psychostimulants, in general, at first increase dopamine transmission and concentration in humans, following which there is a functional reduction in dopaminergic activity. This reduction results in a craving for more psychostimulant, as a means of increasing dopamine and relieving the desire for the drug.

In the present invention, it has been found that psychostimulant abuse can be treated by administering to a human abuser a dopamine agonist in an amount which is effective in inhibiting or eliminating the need for the drug during and after withdrawal. More particularly, it has been found that the withdrawal symptoms resulting from the abrupt cessation of chronic high dose use of psychostimulants can be significantly reduced or eliminated by the administration of an effective amount of a dopamine agonist. The dopamine agonist can be any dopamine stimulating agent, such as, levodopa, bromocriptine, bupropion, pergolide, lisuride and lergotrile, to name a few. The preferred dopamine agonist in the invention is bromocriptine. The amount of agonist administered will vary depending on the active agent used and the patient undergoing treatment. Essentially it will be the same as the known therapeutic dosage. It has however been surprisingly found that particularly good results are obtained in the majority of cases with daily dosages significantly lower than those administered for their known indications. The therapeutically effective amount of levodopa is from 0.5 to 1.0 gram per day. Bromocriptine is generally administered in dosages ranging from 0.1 to 10 milligrams per day. Pergolide and lisuride are effective at daily doses of about 0.05 to 1.0 milligram. Generally, the daily dosage for the ergolene and ergoline type dopamine agonist will be from about 0.05 to about 20 milligrams per day. The daily dosage for non-ergoline type agonists will normally be from 5 to 1000 milligrams per day. The agonist can be administered on a set schedule, for example, every 4 to 6 hours, or it can be administered in accordance with the patient's requirement. The preferred agonist, bromocriptine, is administered in unit doses of about 0.5 to 2.5 milligrams 2 to 4 times daily, preferably about 0.5 to 1.0 milligram 2 to 3 times daily. Normally, a unit dose of about 0.5 to 1 milligram of bromocriptine as required is sifficient to reduce or eliminate the desire for the psychostimulant being abused. It will be appreciated that such doses are significantly lower than those administered for the known indications of this drug, which range from about 2.5 to about 50 milligrams daily.

When appropriate, the dopamine agonist used in the invention may be employed in free base form or in pharmaceutically acceptable salt form. The various ergolene derivatives referred to above may, for example, be used in the form of the mesylate or hydrochloride salt. Generally, the activities of such salt forms will be of the same order as that of the corresponding free base form, and references to compounds in the free base form throughout the specification and claims are to be understood as including known salt forms.

The active agent of the invention may be administered orally or parenterally as such or admixed with conventional pharmaceutical carriers. They may be administered orally in such forms as tablets, dispersible powders, granules, capsules, syrups and elixirs, or parenterally as solutions, e.g., a sterile injectable aqueous solution. Tablets may contain the active ingredients in admixture with conventional pharmaceutically acceptable excipients, e.g., inert diluents and granulating, disintegrating and lubricating agents. The tablets may be uncoated or coated by known techniques to delay disintegration and absorption in the gastrointestinal tract and thereby provide a sustained action over a longer period. Similarly, suspensions, syrups and elixirs may contain the active ingredients in admixture with any of the conventional excipients utilized in the preparation of such compositions. Capsules may contain the active ingredients alone or admixed with an inert solid diluent. The injectable compositions are formulated as known in the art. These pharmaceutical preparations may contain up to about 90% of the active ingredients in combination with the carrier or adjuvant.

Pharmaceutical compositions containing the most preferred compound, bromocriptine mesylate, at dosages of 2.5 and 5 milligrams and suitable for oral administration in accordance with the method of the invention are commercially available. The tablet form is readily broken in half or into quarters for administration of lower doses. Preferably quarters of the 2.5 milligram form are administered 2 to 3 times a day. Alternatively unit dosage forms containing equivalent dosages, e.g. 0.5 milligrams may be employed.

In one patient study, nine patients, four male and five female, ranging in age from 18 to 34, were treated for cocaine withdrawal symptoms with commercially available bromocriptine mesylate. The average length of addiction was four years. Approximately one hour after the last use of the drug, abstinence symptoms began, and reached their peak in three days. After admission to the study, the nine patients were given 0.625 milligrams p.o. of bromocriptine mesylate. The withdrawal symptoms subsided in all patients for periods ranging from 4.5 to 6 hours. Repeated dosing for 1 to 2 weeks permitted the patients to remain free of the most serious symptoms and eventually to enter the group therapy stage of the recovery program.

In a second study, two female in-patients, ages 18 and 20, gave informed consent to receive either bromocriptine or placebo. Both patients were contemplating leaving the hospital to use cocaine; and each complained of depressed mood, anergia, suicidal ideation, and poor concentration. The diagnosis of cocaine abuse was established after a complete evaluation and comprehensive testing to rule out other drug abuse and any medical illness. The patients were asked to rate the degree of craving for cocaine by marking a 100 millimeter line anywhere between "not at all" and "extreme". Scores were assigned according to the point marked, ranging between 0 and 100. Craving was again self-rated at varying time points after 0.625 milligrams p.o. of bromocriptine mesylate or placebo were administered blindly. The results of the cocaine urge self rating before and after placebo or bromocriptine administration is shown in FIG. 1. As can be seen from the figure, both patients reported marked and consistent relief from cocaine craving after taking bromocriptine. In patient No. 1, the cocaine urge self rating dropped from about 60 to about 5 in two hours upon administration of the bromocriptine. In patient No. 2, the cocaine urge self rating dropped from about 75 to about 20 in 90 minutes upon administration of bromocriptine in one rating session, and from about 50 to about 5 in 75 minutes in another session. In addition, both patients were able to distinguish bromocriptine from placebo in all six trials. Afterwards, Subject 1 was given the dopamine antagonist, thioridazine, for the treatment of visual hallucinations and reported an acute increase in cocaine craving. When the effect of the dopamine antagonist on cocaine urges was assessed, craving in two trials increased from baseline scores of 7 and 15 to scores of 30 and 70 respectively after 30 minutes. The results of the study show that cocaine withdrawal symptoms are significantly reduced by the administration of a dopamine agonist, while cocaine urges are exacerbated by dopamine antagonists.

In a further study, a patient was treated for amphetamine abuse with commercially available bromocriptine mesylate. Shortly after the last use of amphetamine, abstinence symptoms began. The patient was given 0.625 milligrams p.o. of bromocriptine mesylate, and withdrawal symptoms subsided. Repeated dosing as needed permitted the patient to remain free of the most serious symptoms.

The present invention also provides a pharmaceutical composition containing a dopamine agonist for use in the treatment of psychostimulant addiction.

Tablets having a diameter of 6 millimeters and the following composition may be prepared according to conventional methods and are suitable for use in the treatment of psychostimulant addiction.

| | |
|---|---|
| Bromocriptine mesylate | 0.574 mg |
| Disodium salt of ethylene diamine tetraacetic acid 2H$_2$O | 0.325 mg |
| Silicium dioxide (Aerosil 200) | 0.225 mg |
| Lactose | 71.076 mg |
| Magnesium stearate | 0.450 mg |
| Corn starch | 11.700 mg |
| Maleic acid | 0.650 mg |
| | 85.000 mg |

(0.574 milligrams of bromocriptine mesylate correspond to 0.5 milligrams of the free base form.)

We claim:

1. A method of treating psychostimulant addiction in a human which comprises administering to a human in need of said treatment a pharmaceutically acceptable dopamine agonist in an amount effective to inhibit psychostimulant addiction.

2. A method according to claim 1 of treating withdrawal symptoms resulting from the cessation of psychostimulant use in a human, which comprises administering to a human in need of said treatment a pharmaceutically acceptable dopamine agonist in an amount effective to inhibit psychostimulant withdrawal symptoms.

3. A method according to claim 1 of preventing the need for psychostimulant use after withdrawal in a human, which comprises administering to a human in need of said treatment a pharmaceutically acceptable dopamine agonist in an amount effective to inhibit psychostimulant craving symptoms.

4. A method according to claim 1 in which the psychostimulant is selected from amphetamine, dextroamphetamine, methamphetamine, and pemoline or a pharmaceutically acceptable acid addition salt thereof.

5. A method according to claim 1 in which the dopamine agonist is selected from levodopa, bromocriptine, bupropion, pergolide, lisuride or lergotrile.

6. A method according to claim 5 in which 0.5 to 1.0 gram of levodopa is administered daily.

7. A method according to claim 5 in which 0.1 to 10 milligrams of bromocriptine are administered daily in free base form or in pharmaceutically acceptable acid addition salt form.

8. A method according to claim 7 in which 0.5 to 2.5 milligrams of bromocriptine are administered in free base form or in pharmaceutically acceptable acid addition salt form per unit dose.

9. A method according to claim 7 in which 0.5 to 1.0 milligram of bromocriptine is administered in free base form or in pharmaceutically acceptable acid addition salt form per unit dose.

10. A method according to claim 5 in which 0.05 to 1.0 milligram of pergolide in free base form or in pharmaceutically acceptable acid addition salt form is administered daily.

11. A method according to claim 1 in which the psychostimulant is amphetamine and the dopamine agonist is bromocriptine.

12. A method according to claim 1 in which the psychostimulant is dextroamphetamine and the dopamine agonist is bromocriptine.

13. A method according to claim 1 in which the psychostimulant is methamphetamine and the dopamine agonist is bromocriptine.

14. A method according to claim 1 in which the psychostimulant is pemoline and the dopamine agonist is bromocriptine.

15. A method of treating cocaine abuse in a human which comprises administering to a human in need of said treatment a pharmaceutically acceptable dopamine agonist in an amount effective to inhibit cocaine addiction.

16. A method according to claim 15, of treating withdrawal symptoms resulting from the cessation of cocaine use in a human, which comprises administering to a human in need of said treatment a pharmaceutically acceptable dopamine agonist in an amount effective to inhibit cocaine withdrawal symptoms.

17. A method according to claim 15, of preventing the need for cocaine after withdrawal, which comprises administering to a human in need of said treatment a pharmaceutically acceptable dopamine agonist in an amount effective to inhibit cocaine craving symptoms.

18. A method according to claim 15 in which the dopamine agonist is selected from levodopa, bromocriptine, bupropion, pergolide, lisuride or lergotrile.

19. A method according to claim 18 in which 0.5 to 1.0 gram of levodopa is administered daily.

20. A method according to claim 18 in which 0.1 to 10 milligrams of bromocriptine are administered daily in free base form or in pharmaceutically acceptable acid addition salt form.

21. A method according to claim 20 in which 0.5 to 2.5 milligrams of bromocriptine are administered in free base form or in pharmaceutically acceptable acid addition salt form per unit dose.

22. A method according to claim 20 in which 0.5 to 1.0 milligram of bromocriptine is administered in free base form or in pharmaceutically acceptable acid addition salt form per unit dose.

23. A method according to claim 18 in which 0.05 to 1.0 milligram of pergolide in free base form or in pharmaceutically acceptable acid addition salt form are administered daily.

24. A pharmaceutical composition for use in treating psychostimulant addiction in a human comprising 0.5 to 1.0 milligram of bromocriptine in free base form or in pharmaceutically acceptable acid addition salt form and a pharmaceutically acceptable carrier therefore.

25. A pharmaceutical composition according to claim 14 comprising 0.5 milligram of bromocriptine in free base form or in pharmaceutically acceptable acid addition salt form.

26. A pharmaceutical composition according to claim 24 in the form of a tablet.

27. A method according to claim 1 of treating psychostimulant addiction in a human which comprises adminstering to a human in need of said treatment a pharmaceutically acceptable ergot alkaloid dopamine agonist in an amount effective to inhibit psychostimulant addiction.

28. a method according to claim 27 of treating withdrawal symptoms resulting from the cessation of psychostimulant use in a human, which comprises administering to a human in need of said treatment a pharmaceutically acceptable ergot alkaloid dopamine agonist in an amount effective to inhibit psychostimulant withdrawal symptoms.

29. A method according to claim 27 in which 0.05 to 20 milligrams of the agonist are adminstered daily in free base form or in pharmaceutically acceptable acid addition salt form.

30. A method according to claim 15 of treating cocaine abuse in a human which comprises administering to a human in need of said treatment a pharmaceutically acceptable ergot alkaloid dopamine agonist in an amount effect to inhibit cocaine addiction.

31. A method according to claim 30 of treating withdrawal symptoms resulting from the cessation of cocaine use in a human, which comprises administering to a human in need of said treatment a pharmaecutically acceptable ergot alkaloid agonist in an amount effective to inhibit cocaine withdrawal symptoms.

32. A method according to claim 30 in which 0.05 to 20 milligrams of bromocriptine are administered daily in free base form or in pharmaceutically acceptable acid addition salt form.

* * * * *

UNITED STATES PATENT AND TRADEMARK OFFICE
CERTIFICATE OF CORRECTION

PATENT NO. : 4,935,429
DATED : June 19, 1990
INVENTOR(S) : Charles A. Dackis and Mark S. Gold It is certified that error appears in the above-identified patent and that said Letters Patent is hereby corrected as shown below:

Please cancel claims 24, 25 and 26.

Title page, "32 Claims, 1 Drawing Sheet" should read --29 Claims, 1 Drawing Sheet--.

Signed and Sealed this

Ninth Day of July, 1991

Attest:

HARRY F. MANBECK, JR.

*Attesting Officer*       *Commissioner of Patents and Trademarks*